(12) United States Patent
Qin

(10) Patent No.: US 8,993,336 B1
(45) Date of Patent: Mar. 31, 2015

(54) SULFUR CALIBRATION AND ANALYTICAL REFERENCE GAS FOR PART PER BILLION CONCENTRATION SULFUR MEASUREMENTS

(75) Inventor: Yang Qin, Bellaire, TX (US)

(73) Assignee: Air Liquide America Specialty Gases LLC, Houston, TX (US)

( * ) Notice: Subject to any disclaimer, the term of this patent is extended or adjusted under 35 U.S.C. 154(b) by 0 days.

(21) Appl. No.: 13/464,343

(22) Filed: May 4, 2012

(51) Int. Cl.
| | | |
|---|---|---|
| *G01N 31/22* | (2006.01) | |
| *G01N 31/00* | (2006.01) | |
| *B01D 53/94* | (2006.01) | |
| *B01D 53/00* | (2006.01) | |
| *F01N 3/08* | (2006.01) | |

(52) U.S. Cl.
CPC .............. *B01D 53/94* (2013.01); *F01N 3/0814* (2013.01)
USPC .......................................................... 436/119

(58) Field of Classification Search
CPC ... G01N 31/22; G01N 31/00; B01D 53/9495; F01N 3/0814; F01N 3/085; F01N 3/00
USPC ........................................................ 436/119
See application file for complete search history.

(56) References Cited

U.S. PATENT DOCUMENTS

| | | |
|---|---|---|
| 6,722,182 B1 | 4/2004 | Buettner |
| 7,837,806 B2 | 11/2010 | Benesch et al. |
| 2005/0271544 A1 | 12/2005 | Benesch et al. |

FOREIGN PATENT DOCUMENTS

RU      2405144 C1 * 11/2010   ............. G01N 33/22

OTHER PUBLICATIONS

Duvekot et al., The Analysis of Sulfur Components in Various LPGs—Application Noe SI-01589, www.varianinc.com, 2008, pp. 1-4.*
Bulatov et al, Composition of Standard Samples of Trace Concentrations of Sulphur in Oil and Products From Processing Said Composition, Machine Translation of Description, obtained on Nov. 24, 2014 from Espacenet.*
Bulatov et al, Composition of Standard Samples of Trace Concentrations of Sulphur in Oil and Products From Processing Said Composition, Machine Translation of Claims, obtained on Nov. 24, 2014 from Espacenet.*
Robert Benesch and Tracey Jacksier, "A Comparison of Liquid Hydrocarbon Calibration Standards in Piston Cylinders and Standard Cylinders With Eductor Tubes," Anal. Chem. 2001, 73, 379-383.
Roger L. Firor and Bruce D. Quimby, "Automated Dynamic Blending System for the Agilent 6890 Gas Chromatograph: Low Level Sulfur Detection" (Apr. 2001).
Sudhir Kumar Pandey and Ki-Hyun Kim, "Comparison of Different Calibration Approaches in the Application of Thermal Desorption Technique: A Test on Gaseous Reduced Sulfur Compounds," Microchemical Journal 91 (2009) 40-46.

* cited by examiner

*Primary Examiner* — Christine T Mui
(74) *Attorney, Agent, or Firm* — Allen E. White

(57) ABSTRACT

The invention relates in part to a Sulfur standard gas in the ppb range in a matrix gas. The Sulfur standard gas is maintained in a cylinder under pressure sufficient to compress the majority of the Sulfur gas and into a liquid matrix.

14 Claims, 2 Drawing Sheets

Vaporizer

SULFUR CALIBRATION AND ANALYTICAL REFERENCE GAS FOR PART PER BILLION CONCENTRATION SULFUR MEASUREMENTS

TECHNICAL FIELD

The invention relates to analytical and calibration gases that serve as reference standards for ascertaining the level of sulfur in industrial gases having very low levels of sulfur.

BACKGROUND ART

The measurement of sulfur in the parts per billion (ppb) levels is particularly relevant for liquefied petroleum gas, refinery gas or natural gas (collectively industrial hydrocarbon products). Industrial hydrocarbon products contaminated with even ppb levels of Sulfur can poison catalysts used in industrial hydrocarbon product processing and various fuel cell technologies are sensitive to similar low Sulfur levels. The problem to be solved is the provision of a stable reference gas for use as a calibration and analysis standard in the ppb range.

The state of the art includes some solutions to the problem of ppb Sulfur standard stability. One approach is to perform a sophisticated passivation process which significantly limits the loss of Sulfur to adsorption by container walls. These technologies are provided for many reactive gases under the brand ALPHATECH™. ALPHATECH™ is described in various U.S. patents including U.S. Pat. No. 7,837,806. ALPHATECH™ requires a sophisticated and specialized manufacturing base and this reality translates into a relatively high priced calibration gas product.

A second alternative approach is to avoid the problem by using higher concentration and more stable Sulfur standards to derive a diluted ppb standard on demand.

One example of an on-site dilution approach is the use of permeation tubes to generate low concentration reference gas. U.S. Pat. No. 6,722,182 describes an example of this approach. Permeation tubes generally require precise carrier gas flow control and temperature control. The provision, maintenance and operation of permeation tubes require special software and process integration into an industrial facility that have made use of this technology difficult. {Not adopted in hydrocarbon industrial analysis because of difficulty in using.}

In response to the need for a better solution to the problem, AGILENT™ developed an on site, high precision, blending system. This system is designed to dilute a 5 ppm Sulfur standard down to as low as 20 ppb. R. L. Firor and B. D. Quimby, Automated Dynamic Blending System for the Agilent 6890 Gas Chromatograph: Low Level Sulfur Detection, Publication Number 5988-2465, April 2001. The blending approach has the advantage of using cylinder gas as the source for a diluted ppb Sulfur standard. As with permeation tubes, blending systems still require integration of new equipment into existing industrial settings and processes. The high precision blender technology is also still relatively expensive.

While the art has provided a number of solutions to the problem of providing a reliable ppb level Sulfur gas standard, these solutions all require sophisticated technology that results in substantial cost. Thus, in many circumstances, the only practical option is to prepare fresh standard gases and use these sulfur standards immediately, particularly for ppb level measurements. See, e.g., Sudhir Kumar Pandey, Ki-Hyun Kim, Comparison of different calibration approaches in the application of thermal desorption technique: A test on gaseous reduced sulfur compounds, Microchemical Journal, Volume 91, Issue 1, January 2009, Pages 40-46, ISSN 0026-265X, 10.1016/j.microc.2008.07.004. There is therefore a need in the art for a solution that is both less expensive and less complex in nature. Ideally, the solution would be cylinder gas based such that the gas standard may be pre-certified by the calibration gas vendor. The present invention provides such a solution.

SUMMARY OF INVENTION

Some embodiments of the invention may be understood in relation to the following numbered sentences:

1. A Sulfur reference standard comprising a Sulfur compound at a concentration of 1 to 500 parts per billion in a matrix gas, the Sulfur reference standard being under sufficient pressure and temperature conditions to form a liquid phase having the Sulfur compound concentration of 1 to 500 parts per billion in the liquid phase.
2. The Sulfur reference standard of sentence 1, wherein the concentration of the Sulfur compound is from 50 to 100 parts per billion.
3. The Sulfur reference standard of sentence 1, wherein the concentration of the Sulfur compound is from 100 to 200 parts per billion.
4. The Sulfur reference standard of sentences 1, 2, or 3, wherein the matrix gas comprises one or more three and/or four carbon containing hydrocarbon.
5. The Sulfur reference standard of sentences 1, 2, 3 or 4 wherein
   a) the Sulfur compound comprises one or more Sulfur component selected from hydrogen sulfide, carbonyl sulfide, carbon disulfide, dimethyl sulfide, t-butyl mercaptan, and tetrahydrothiophene, $C_1$-$C_5$ mercaptan, or dimethyl disulfide, diethyl disulfide;
   b) the matrix gas comprises propylene and/or butane; and
   c) each Sulfur component is at a concentration of 50-200 ppb in the matrix gas.
6. A cylinder comprising the Sulfur reference standard of sentences 1, 2, 3, 4 or 5.
7. The cylinder of sentence 6, wherein the cylinder comprises a surface passivated for at least one Sulfur compound in the Sulfur reference standard.
8. The cylinder of sentence 6, further comprising a vaporizer in fluid communication with the cylinder and configured to vaporize the Sulfur reference standard into a gas having a predetermined temperature, the predetermined temperature corresponding to a temperature suitable for a calibration or analytical process.
9. The cylinder of sentences 6, 7, or 8 wherein the cylinder is a piston cylinder.
10. The cylinder of sentences 6, 7, or 8, further comprising a pressurizing headspace gas.
11. The cylinder of sentence 10, wherein the headspace gas comprises Helium.
12. A method of calibrating an instrument for the measurement of a Sulfur compound at parts per billion level, the method comprising the steps of providing the Sulfur reference standard of sentence 1 to an instrument and performing a measurement of the Sulfur content of the Sulfur reference standard.
13. The method of sentence 12, wherein the instrument comprises a gas chromatography separation device, a thermal desorption device, and a Pulsed Flame Photometric Detector or a Sulfur Chemiluminescence Detector.
14. A method of measuring a Sulfur compound at parts per billion level, the method comprising the steps of providing the Sulfur reference standard of sentence 1 to an instrument and performing a measurement of the Sulfur content of the Sulfur reference standard and a test sample representing a gas with an unknown level of the Sulfur compound(s) in the Sulfur reference standard.

15. The method of sentence 14, wherein the test sample represents an industrial hydrocarbon gas.

DISCLOSURE OF INVENTION

The invention relates in part to a Sulfur standard gas in the ppb range in a matrix gas. The Sulfur standard gas is maintained in a cylinder under pressure sufficient to compress the Sulfur gas and matrix gas into a liquid state. Samples of the liquid phase Sulfur/matrix composition are removed as a liquid and vaporized to a gaseous state having a temperature compatible with the analytic or calibration process being used. By maintaining the Sulfur/matrix composition as a liquid, the rate of absorption onto the cylinder surface is dramatically reduced. An unpassivated aluminum cylinder is stable as a certified ppb Sulfur standard for approximately one month. Cylinder passivation may be used to extend the shelf life of a standard. See for example ALPHATECH™ cylinder passivation as described in U.S. Pat. Nos. 7,832,550; 7,837,806; 7,794,841; 7,799,150 and 7,850,790. An ALPHATECH™ passivated cylinder can extend cylinder shelf life to at least one year. An unpassivated cylinder with liquefied ppb Sulfur in a matrix gas can last as a certified standard for an estimated minimum of four years. Storing the ppb Sulfur standard as a liquid in an ALPHATECH™ cylinder is expected to extend the certified standard's shelf life to a virtual indefinite length of time.

MODE(S) FOR CARRYING OUT THE INVENTION

Sulfur Standard Cylinder

Figure 1:
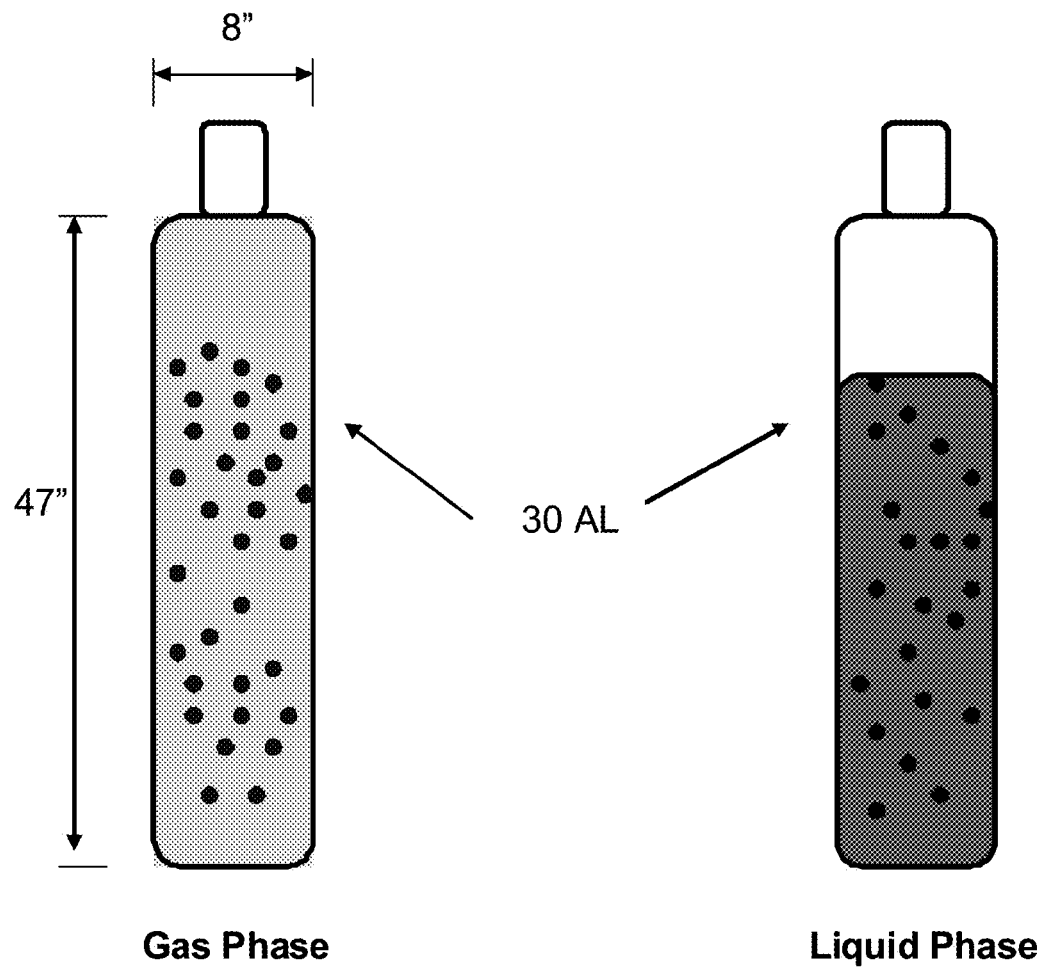
FIG. 1 shows a representation of a liquid Sulfur/matrix standard of the invention.
Figure 2:
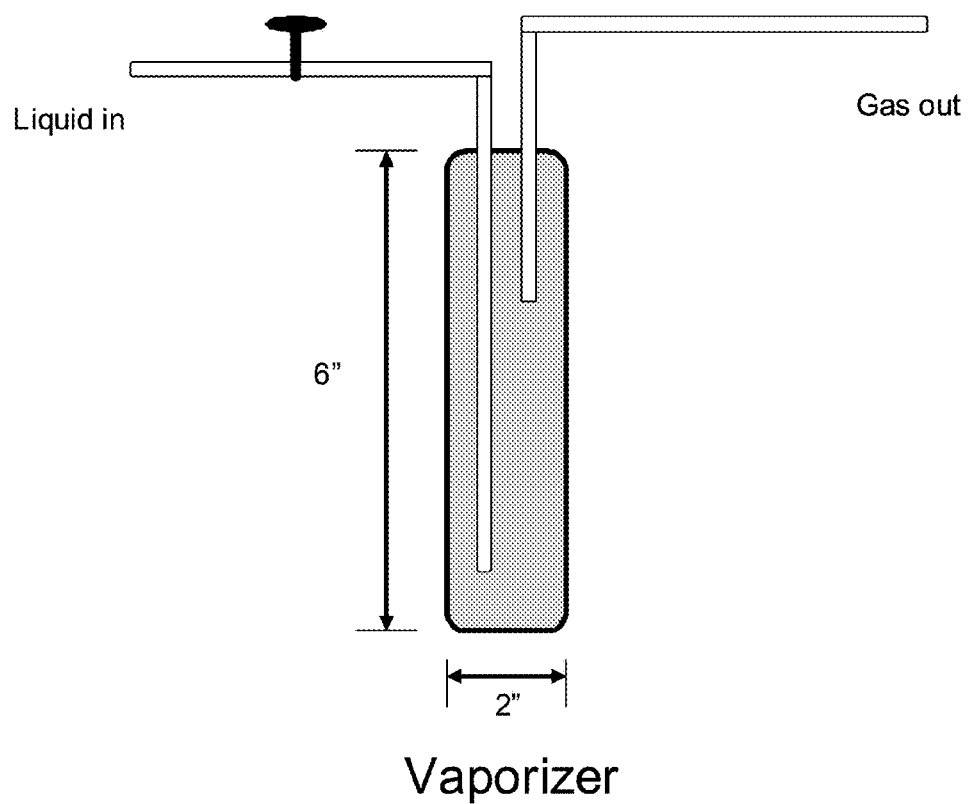
FIG. 2 shows an exemplary schematic of a vaporizer for converting the liquid standard into a useable gaseous state.

FIG. 1 on the left illustrates the state of the art. To ensure a homogeneous gas phase, about 210 gram or 5 moles of propylene is allowed to put in a 30 AL cylinder for a sulfur standard mixture. In a standard condition, 5 mole gas has a volume 112 liters. If we this standard is used to calibrate 2 hours every day at a typical flow rate of 30 sccm, the standard can only last for one month.

For liquid phase propylene (FIG. 1 on the right), one is able to put 9000 gram or 214 mole of propylene in a 30 AL cylinder to make 200 ppb sulfur ($42*10^{-6}$ mole) standard. Vaporizing to a gas phase, this corresponds to 4800 liters of gas in standard condition. As a sample flow rate of 30 SCCM for 2 hours per day, this cylinder would last at least 4 years.

The sulfur standard cylinder is pressurized with Helium, or any another suitable headspace gas, or combination thereof, to create a headspace pressure sufficient to maintain the sulfur standard in liquid form. If the minimum amount of Helium is used to pressurize a full cylinder, the headspace pressure will diminish as liquid is withdrawn from the cylinder. Headspace pressure thus should compensate for draw down of the cylinder contents to maintain a liquid phase for at least the full amount of sulfur standard that the cylinder is intended to provide.

Overhead pressure may be maintained through use cycle of the cylinder a number of ways. The simplest method is to over pressurize the initial cylinder headspace such that the pressure is sufficient to maintain a liquid phase throughout the cylinder use cycle. For example, the headspace gas may be sufficient to result in a 240 psig pressure at the end of the cylinder use cycle. This option will use more headspace gas, which is of particular concern where Helium is used.

An alternative is to use a piston cylinder as is known in the art for hydrocarbon standards. See, e.g., Robert Benesch and Tracey Jacksier, "A Comparison of Liquid Hydrocarbon Calibration Standards in Piston Cylinders and Standard Cylinders with Eductor Tubes", Analytical Chemistry 2001 73 (2), 379-383. The piston cylinder option maintains a stable pressure throughout the cylinder use cycle and eliminates the need for Helium or other headspace gas. Other techniques include repressurizing the sulfur standard cylinder with supplemental headspace gas at different stages of the use cycle based on the cylinder pressure as indicated by a pressure gauge. Many other possibilities exist to maintain the liquid phase of the sulfur standard. Any suitable pressurization technique is acceptable.

Vaporization

Depending on the analytical equipment and requirements, the liquid sulfur standard may be vaporized a number of ways to provide a gas phase standard. Generally, devices designed to vaporize liquids for GC analysis are well know in the art and widely available. In gas chromatography (GC) analysis, the GC may have an integrated vaporizer. For example, Agilent® developed a large volume injection programmable temperature vaporizer suitable for receiving liquid sulfur standard directly from a cylinder. Other commercial alternatives include the VARIAN® Micro-Gassifier system.

In on embodiment, the sulfur standard cylinder is equipped with a liquid dispensing device with or without an associated vaporizer. Generally, a liquid inlet valve such as a needle valve is used to control the liquid amount introduced into the vaporizer. To ensure a constant gas flow through entire sampling system, a GC injection system generally should include a flow meter and the flow rate of gas phase sulfur standard may be maintained at a flow rate of 30 cc/m. Analytical systems suitable for sulfur content analysis are well known in the art and commercially available. An Example is a Varian/Agilent® GC systems equipped with a Sievers® 355 Sulfur Chemiluminescence Detector (SCD) and Agilent® DB-1 (Dimethylpolysiloxane gum; USP G2) column. Sulfur analysis is performed according to existing procedures well established in the state of the art.

INDUSTRIAL APPLICABILITY

The present invention is at least industrially applicable to calibrated analytical measurements of ppb levels of Sulfur compounds in industrial hydrocarbon products.

The invention claimed is:

1. A cylinder comprising a Sulfur reference standard, the Sulfur reference standard comprising a Sulfur compound at a concentration of 1 to 500 parts per billion in a matrix gas, the Sulfur reference standard being under sufficient pressure and temperature conditions to form a matrix liquid phase having the Sulfur compound concentration of 1 to 500 parts per billion in the liquid phase, wherein the matrix liquid phase comprises one or more three and/or four carbon containing hydrocarbon.

2. The cylinder comprising the Sulfur reference standard of claim 1, wherein the concentration of the Sulfur compound is from 50 to 100 parts per billion.

3. The cylinder comprising the Sulfur reference standard of claim 1, wherein the concentration of the Sulfur compound is from 100 to 200 parts per billion.

4. The cylinder comprising the Sulfur reference standard of claim 1 wherein
   a) the Sulfur compound comprises one or more Sulfur component selected from hydrogen sulfide, carbonyl sulfide, carbon disulfide, dimethyl sulfide, t-butyl mercaptan, and tetrahydrothiophene, $C_1$-$C_5$ mercaptan, or dimethyl disulfide, diethyl disulfide;
   b) the matrix liquid phase comprises propylene and/or butane; and
   c) each Sulfur component is at a concentration of 50-200 ppb in the matrix gas.

5. The cylinder of claim 1, wherein the cylinder comprises a surface passivated for at least one Sulfur compound in the Sulfur reference standard.

6. The cylinder of claim 4, wherein the cylinder comprises a surface passivated for at least one Sulfur compound in the Sulfur reference standard.

7. The cylinder of claim 1, further comprising a vaporizer in fluid communication with the cylinder and configured to vaporize the Sulfur reference standard into a gas having a predetermined temperature, the predetermined temperature corresponding to a temperature suitable for a calibration or analytical process.

8. The cylinder of claim 1, wherein the cylinder is a piston cylinder.

9. The cylinder of claim 1, further comprising a pressurizing headspace gas.

10. The cylinder of claim 9, wherein the headspace gas comprises Helium.

11. A method of calibrating an instrument for the measurement of a Sulfur compound at parts per billion level, the method comprising the steps of providing the cylinder comprising the Sulfur reference standard of claim 1 to an instrument and performing a measurement of the Sulfur content of the Sulfur reference standard.

12. The method of claim 11, wherein the instrument comprises a gas chromatography separation device, a thermal desorption device, and a Pulsed Flame Photometric Detector or a Sulfur Chemiluminescence Detector.

13. A method of measuring a Sulfur compound at parts per billion level, the method comprising the steps of providing the cylinder comprising the Sulfur reference standard of claim 1 to an instrument and performing a measurement of the Sulfur content of the Sulfur reference standard and a test sample representing a gas with an unknown level of the Sulfur compound(s) in the Sulfur reference standard.

14. The method of claim 13, wherein the test sample represents an industrial hydrocarbon gas.

\* \* \* \* \*